United States Patent
Hadani et al.

(10) Patent No.: US 9,820,719 B2
(45) Date of Patent: Nov. 21, 2017

(54) METHOD AND SYSTEM FOR INTRABODY IMAGING

(75) Inventors: Ron Hadani, Cresskill, NJ (US); Mark Landman, Sharon, MA (US)

(73) Assignee: COGENTIX MEDICAL, INC., Minnetonka, MN (US)

( * ) Notice: Subject to any disclaimer, the term of this patent is extended or adjusted under 35 U.S.C. 154(b) by 150 days.

(21) Appl. No.: 13/330,950

(22) Filed: Dec. 20, 2011

(65) Prior Publication Data

US 2012/0089028 A1   Apr. 12, 2012

Related U.S. Application Data

(63) Continuation-in-part of application No. 12/486,795, filed on Jun. 18, 2009, now abandoned.

(60) Provisional application No. 61/129,344, filed on Jun. 19, 2008.

(51) Int. Cl.
| | |
|---|---|
| *A61B 8/12* | (2006.01) |
| *A61B 8/14* | (2006.01) |
| *A61B 8/00* | (2006.01) |
| *A61B 1/00* | (2006.01) |
| *A61B 1/018* | (2006.01) |

(52) U.S. Cl.
CPC .............. *A61B 8/12* (2013.01); *A61B 8/14* (2013.01); *A61B 8/445* (2013.01); *A61B 8/58* (2013.01); *A61B 1/00098* (2013.01); *A61B 1/018* (2013.01)

(58) Field of Classification Search
CPC ....... A61B 8/14; A61B 1/00098; A61B 1/018; A61B 8/12; A61B 8/445; A61B 8/58
USPC ................................... 600/407–480
See application file for complete search history.

(56) References Cited

U.S. PATENT DOCUMENTS

| | | |
|---|---|---|
| 4,364,629 A | 12/1982 | Lang et al. |
| 4,406,656 A | 9/1983 | Hattler et al. |
| 4,646,722 A | 3/1987 | Silverstein et al. |
| 4,676,228 A | 6/1987 | Krasner et al. |
| 4,773,396 A | 9/1988 | Okazaki |
| 4,841,952 A | 6/1989 | Sato et al. |
| 4,856,495 A | 8/1989 | Tohjoh et al. |
| 5,025,778 A | 6/1991 | Silverstein et al. |
| 5,083,549 A | 1/1992 | Cho et al. |
| 5,166,787 A | 11/1992 | Irion |

(Continued)

FOREIGN PATENT DOCUMENTS

| | | |
|---|---|---|
| EP | 2011431 A1 | 1/2009 |
| WO | WO 95/18562 A1 | 7/1995 |

(Continued)

OTHER PUBLICATIONS

Official Action dated Jan. 25, 2013 From U.S. Appl. No. 12/486,795.

(Continued)

*Primary Examiner* — Vani Gupta

(74) *Attorney, Agent, or Firm* — Dorsey & Whitney LLP

(57) ABSTRACT

A catheter that comprises a catheter configured for housing at least a portion of a catheter configured for insertion into a body lumen in proximity of a targeted anatomical site and having an imager at a distal end thereof and an adjustable chamber configured for covering the imager. The catheter is configured for introducing a wave conductive medium to the adjustable chamber to increase wave conductivity between said targeted anatomical site and the imager.

21 Claims, 5 Drawing Sheets

(56) References Cited

U.S. PATENT DOCUMENTS

| | | |
|---|---|---|
| 5,167,220 A | 12/1992 | Brown |
| 5,201,908 A | 4/1993 | Jones |
| 5,217,001 A | 6/1993 | Nakao et al. |
| 5,305,736 A | 4/1994 | Ito |
| 5,377,688 A | 1/1995 | Aviv et al. |
| 5,460,168 A | 10/1995 | Masubuchi et al. |
| 5,483,951 A | 1/1996 | Frassica et al. |
| 5,489,256 A | 2/1996 | Adair |
| 5,503,616 A | 4/1996 | Jones |
| 5,588,432 A | 12/1996 | Crowley |
| 5,749,889 A | 5/1998 | Bacich et al. |
| 5,810,776 A | 9/1998 | Bacich et al. |
| 5,823,940 A | 10/1998 | Newman |
| 5,842,973 A | 12/1998 | Bullard |
| 5,940,126 A | 8/1999 | Kimura |
| 5,961,445 A | 10/1999 | Chikama |
| 5,966,168 A | 10/1999 | Miyazaki |
| 5,989,185 A | 11/1999 | Miyazaki |
| 6,095,970 A | 8/2000 | Hidaka et al. |
| 6,146,326 A | 11/2000 | Pollack et al. |
| 6,174,280 B1 | 1/2001 | Oneda et al. |
| 6,358,200 B1 | 3/2002 | Grossi |
| 6,443,968 B1 | 9/2002 | Holthaus et al. |
| 6,461,294 B1 | 10/2002 | Oneda et al. |
| 6,579,301 B1 | 6/2003 | Bales et al. |
| 6,692,431 B2 | 2/2004 | Kazakevich |
| 6,740,030 B2 | 5/2004 | Martone et al. |
| 6,761,685 B2 | 7/2004 | Adams et al. |
| 6,808,520 B1 | 10/2004 | Fourkas et al. |
| 6,827,710 B1 | 12/2004 | Mooney et al. |
| 7,044,135 B2 | 5/2006 | Lesh |
| 7,410,462 B2 | 8/2008 | Navok et al. |
| 7,753,842 B2 | 7/2010 | Glukhovsky et al. |
| 7,883,468 B2 * | 2/2011 | Makin ............... A61N 7/022 600/447 |
| 8,002,699 B2 | 8/2011 | Hoefig |
| 8,435,170 B2 | 5/2013 | Wood et al. |
| 2001/0000040 A1 | 3/2001 | Adams et al. |
| 2003/0130564 A1 | 7/2003 | Martone et al. |
| 2003/0167023 A1* | 9/2003 | Bennett et al. .............. 601/2 |
| 2004/0019254 A1 | 1/2004 | Belson et al. |
| 2004/0092821 A1* | 5/2004 | Hering ............... A61B 8/12 600/459 |
| 2004/0143162 A1 | 7/2004 | Krattiger et al. |
| 2004/0230095 A1 | 11/2004 | Stefanchik et al. |
| 2004/0230096 A1 | 11/2004 | Stefanchik et al. |
| 2005/0049455 A1 | 3/2005 | Ootawara et al. |
| 2005/0131278 A1 | 6/2005 | Dickopp |
| 2005/0182299 A1 | 8/2005 | D'Amelio et al. |
| 2005/0261586 A1* | 11/2005 | Makin et al. ............ 600/459 |
| 2006/0149127 A1 | 7/2006 | Seddiqui et al. |
| 2006/0264705 A1 | 11/2006 | Adams et al. |
| 2007/0265494 A1 | 11/2007 | Leanna et al. |
| 2007/0293719 A1 | 12/2007 | Scopton et al. |
| 2010/0042112 A1 | 2/2010 | Qureshi et al. |
| 2011/0152618 A1 | 6/2011 | Surti |
| 2014/0364691 A1 | 12/2014 | Krivopisk et al. |
| 2015/0031947 A1 | 1/2015 | Kudo et al. |

FOREIGN PATENT DOCUMENTS

| | | |
|---|---|---|
| WO | WO 2005/016181 A2 | 2/2005 |
| WO | WO 2007/103296 A2 | 9/2007 |
| WO | WO 2007/103355 A1 | 9/2007 |

OTHER PUBLICATIONS

Olympus "Evis Exera Duodenovideoscope Olympus TJF Type 160VF, LinearGuideV", Product Description, Olympus Corporation, 2 P.

Official Action dated Apr. 27, 2012 From U.S. Appl. No. 12/486,795.

Official Action dated Aug. 20, 2013 From U.S. Appl. No. 12/486,795.

Restriction Official Action dated Feb. 29, 2012 From U.S. Appl. No. 12/486,795.

Official Action dated Feb. 7, 2014 From U.S. Appl. No. 12/486,795.

The International Search Report and Written Opinion dated Oct. 4, 2016 in connection with International Patent Application No. PCT/US16/42062, 11 pages.

The extended European Search Report dated Mar. 27, 2015 in connection with European Patent Application No. 14198653.9, 8 pages.

Communication Pursuant to Article 94(3) dated Jul. 19, 2011 in connection with European Patent Application No. 04780129.5, 7 pages.

Communication Pursuant to Article 94(3) dated Feb. 21, 2011 in connection with European Patent Application No. 04780129.5, 9 pages.

International Preliminary Report on Patentability dated Feb. 15, 2006 in connection with International Patent Application No. PCT/US04/25238, 14 pages.

International Search Report and Written Opinion dated Feb. 14, 2005 in connection with International Patent Application No. PCT/US04/25238, 7 pages.

Supplementary European Search Report dated Apr. 20, 2010 in connection with European Patent Application No. 04780129.5, 3 pages.

Communication Pursuant to Article 94(3) dated Aug. 6, 2014 in connection with European Patent Application No. 08163701.9, 4 pages.

European Search Report dated Oct. 21, 2008 in connection with European Patent Application No. 08163701.9, 5 pages.

Communication Pursuant to Article 94(3) dated Jun. 5, 2012 in connection with European Patent Application No. 08163701.9, 4 pages.

Communication Pursuant to Article 94(3) dated Sep. 25, 2009 in connection with European Patent Application No. 08163701.9, 4 pages.

* cited by examiner

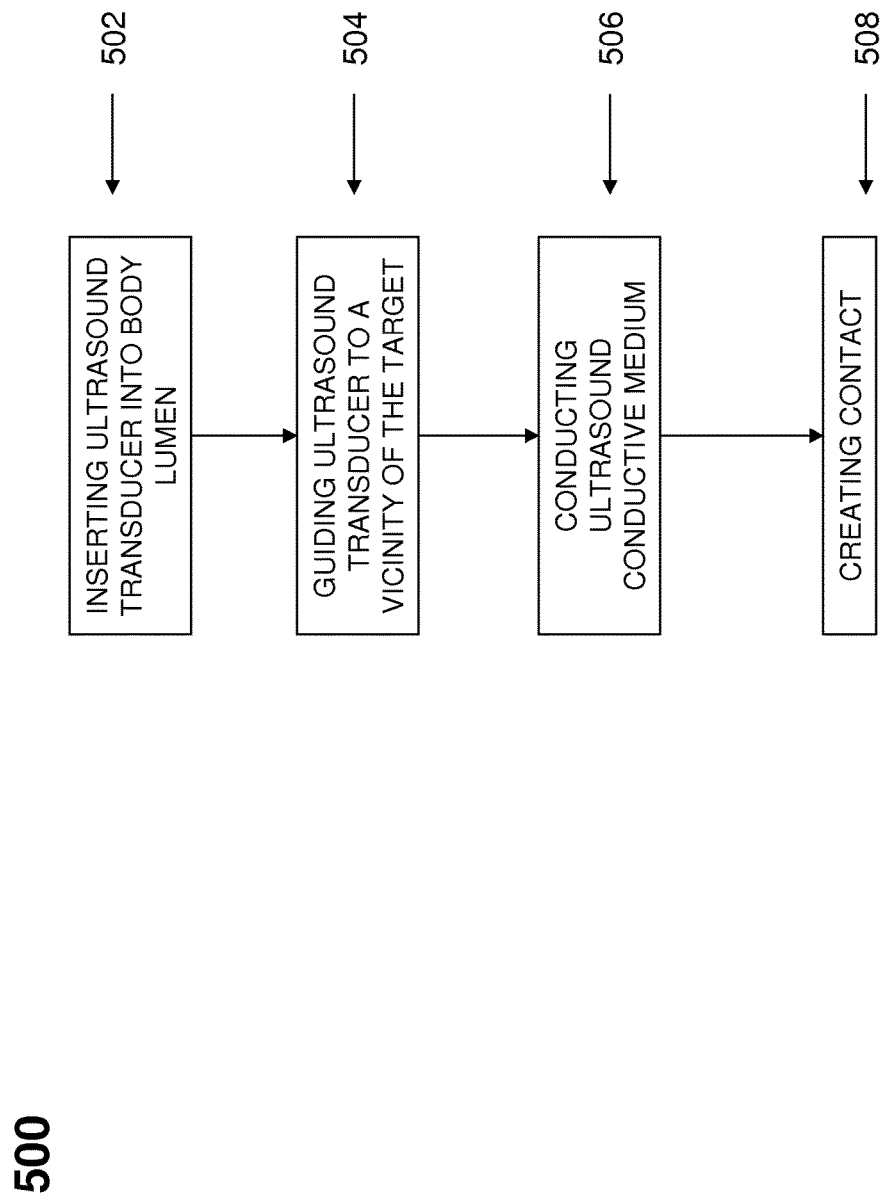

METHOD AND SYSTEM FOR INTRABODY IMAGING

RELATED APPLICATIONS

This application is a continuation-in-part (CIP) of U.S. patent application Ser. No. 12/486,795 filed Jun. 18, 2009, which claims the benefit of priority under 35 USC 119(e) of U.S. Provisional Patent Application No. 61/129,344 filed Jun. 19, 2008.

The contents of the above applications are incorporated herein by reference in their entirety.

FIELD AND BACKGROUND OF THE INVENTION

The present invention, in some embodiments thereof, relates to medical devices and, more particularly, but not exclusively, to catheters, endoscopes, endoscopic tools, and intrabody probes.

Endoscopy is a minimally invasive diagnostic medical procedure that is used to assess the interior surfaces of an organ or of a body by inserting an insertion tube of an endoscope into a body lumen, or cavity, of a patient. A typical endoscope includes a rigid or flexible endoscopic insertion tube and an endoscope control unit, such as a handle, for allowing a user to hold and/or control the endoscopic insertion tube, to manipulate the endoscopic insertion tube in the body, to angulate the tip of the endoscope, and to control video functions such as image capture and image freeze frame. The endoscopic insertion tube is usually associated with an imaging sensor, designed to provide an image of the body lumen for visual inspection and photography. Frequently-used image capturing devices are: an ultrasound imager, fiber optics and video cameras.

Minimally invasive surgical procedures avoid open invasive surgery in favor of closed or local surgery with fewer traumas. These procedures typically involve remote-control manipulation of endoscopic tools with observation of the surgical field through an endoscope or similar device, and are carried out through the skin or through a body lumen or anatomical opening, or a combination of the above. Endoscopic tools are elements for treating and/or probing targeted anatomic sites in body lumens. There exist many kinds of endoscopic tools, each endoscopic tool having a specific function or a limited number of functions. Common examples of endoscopic tools are needles, used for injecting substances into targeted anatomic site tissues or obtaining a tissue sample, biopsy forceps, used to remove one or more tissue samples for analysis, and endoscopic graspers for grasping slippery tissue or foreign bodies. Endoscopic tools and medical imagers are also referred to as "tools", "medical tools" or "endoscope tools" in the art.

In order for an ultrasound transducer to provide a clear image of a targeted anatomic site in a body lumen, the ultrasound device has to be in direct contact with the targeted anatomic site or a wave conductive medium has to be positioned between the ultrasound transducer and the targeted anatomic site. A known procedure for allowing ultrasound imaging involves filling the body lumen in which the sensor is inserted with an ultrasound conductive medium. Such a procedure, however, may cause discomfort to the patient whose lumen is being probed. Solutions have been proposed to allow ultrasonic imaging without filling the lumen with ultrasound conductive medium.

In U.S. Pat. No. 6,402,695 by Grimm, an ultrasound probe cover is provided, which includes a conventional inflatable bag adapted to fit over an ultrasound probe. The inflatable bag is filled with an ultrasound conductive medium and then secured to the probe through an external securing element, before the probe is inserted into the body lumen. As the filling takes place before the insertion of the probe into the cover, a user must be careful not to spill the ultrasound conductive medium out of the cover while inserting the probe into the cover. Thus, the above cover may be difficult to use.

In U.S. Pat. No. 5,335,663 by Oakley et al., and U.S. Pat. No. 5,469,853 by Law et al., a removable, rigid sheath is provided to fit over a laparoscopic probe. The removable sheath optionally includes a balloon tip that can be inflated with ultrasound conductive medium, and a lumen for injecting ultrasound conductive medium in the vicinity of an ultrasonic device linked to the probe inserted into the sheath.

SUMMARY OF THE INVENTION

The present invention, in some embodiments thereof, relates to increasing wave conductivity to allow imaging of a targeted anatomic site in a body by an imager, such as an ultrasound transducer which is connected to the distal end of an intrabody guiding tube, such as a catheter which is designed to pass in a working channel of an endoscope. The channel, through which the ultrasound transducer is passed, is covered with an adjustable chamber, which may be filled with an ultrasound conductive medium while inside the body lumen. The flexibility coefficient of the walls of the adjustable chamber may be substantially constant. The adjustable chamber may fit a working channel of an endoscope. The filling adjusts the volume of the adjustable chamber to match the size and shape of the body lumen.

According to some embodiments of the present invention, there are provided a device for passage of an ultrasound catheter having an ultrasound imager at the distal end thereof, the ultrasound catheter. The device comprises a catheter configured for covering at least a portion of the ultrasound catheter, and an adjustable chamber configured for covering the ultrasound imager. The adjustable chamber being configured for being adjusted by a wave conductive medium introduced thereto via the catheter.

Optionally, the catheter is a disposable sheath configured for containing an endoscopic tool.

Optionally, the catheter is configured for insertion into a body lumen in proximity to a targeted anatomical site, the adjustable chamber is configured for being stretched to increase wave conductivity in a space between the targeted anatomic site and the imager.

Optionally, the adjustable chamber is made of a non stretchable material and configured for being inflated to increase wave conductivity in a space between a targeted anatomic site and the imager.

More optionally, the wave conductivity is increased by reducing the space between an outer surface of the adjustable chamber and at least one inner wall of the body lumen.

More optionally, the imager comprises at least one ultrasound transducer and the wave conductivity being an ultrasonic conductivity.

Optionally, the adjustable chamber is detachable from the catheter.

Optionally, the catheter is disposable.

Optionally, the adjustable chamber and the catheter are integrally formed.

Optionally, the device further comprises a separate conduit configured for introducing the conductive medium.

Optionally, the catheter is configured for allowing the traversing of an endoscopic tool therethrough, further comprising a tool deflector configured for deflecting the endoscopic tool by changing a direction of movement of the endoscopic tool in relation to a direction of movement of the distal end.

More optionally, the endoscopic tool traverses the catheter through a sheath channel located on a surface of the catheter and configured for preventing puncturing the adjustable chamber by the endoscopic tool.

Optionally, the device further comprises a mechanism configured for reducing the amount of gas in the adjustable chamber.

According to some embodiments of the present invention, there is provided a method for imaging a targeted anatomic site within a body lumen. The method comprises guiding a catheter with a distal end having an imager and an adjustable chamber covering at least a portion of the imager toward the targeted anatomic site via a body lumen, increasing wave conductivity between at least one inner wall of the body lumen and the imager, and using the imager for imaging the targeted anatomic site through the wave conductive medium and the adjustable chamber.

Optionally, the increasing comprises reducing a space between an outer surface of the adjustable chamber and at least one inner wall of a body lumen in proximity to the targeted anatomic site.

Optionally, the increase is a product of establishing a physical contact between at least one inner wall of the body lumen and the adjustable chamber.

Optionally, the imager comprises at least one ultrasound transducer and the wave conductivity being an ultrasonic conductivity.

According to some embodiments of the present invention, there is provided an endoscope for imaging an anatomic site in proximity to a body lumen. The endoscope comprises a catheter having an opened distal end and configured for insertion into the body lumen and passage of an ultrasound imager and a wave conductive medium therethrough, and an adjustable chamber configured for covering at least the opened distal end by an adjustable portion. The adjustable chamber is configured for being filled with the wave conductive medium to increase wave conductivity in a space between the anatomic site and the imager.

Optionally, the endoscope further comprises a pressure device for controlling the wave conductive medium.

Optionally, the adjustable chamber is configured for being attached in a detachable manner to the catheter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 is a flowchart illustrating a method for imaging a targeted anatomic site by directing an imager within a body lumen, according to some embodiments of the present invention.

DESCRIPTION OF SPECIFIC EMBODIMENTS OF THE INVENTION

Figure 1:
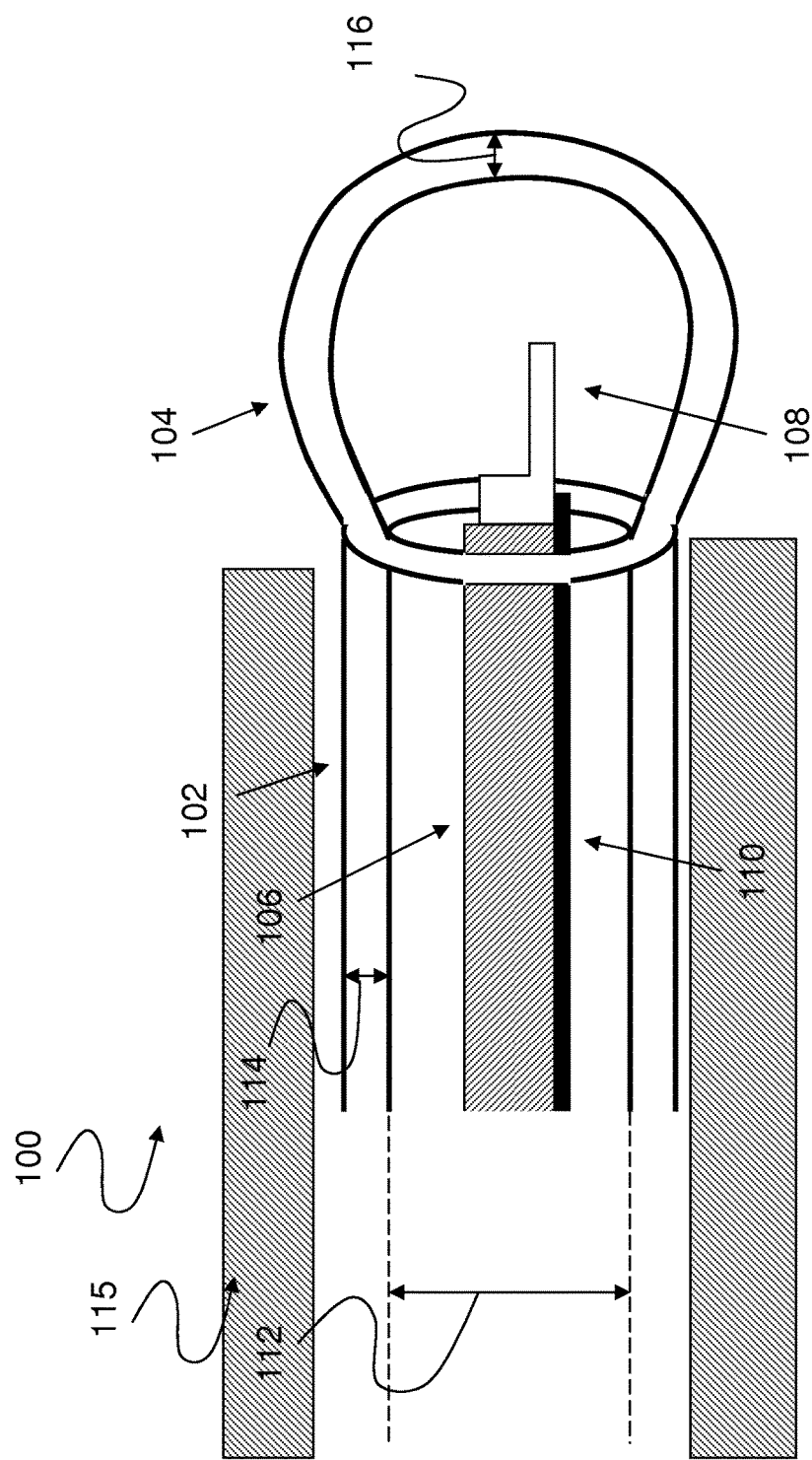
FIG. 1 is a schematic illustration of a tip of a catheter characterized by an adjustable chamber, which is designed to be filled by a wave conductive medium, according to some embodiments of the present invention.

The present invention, in some embodiments thereof, relates to medical devices and, more particularly, but not exclusively, to catheters, endoscopes, endoscopic tools, and intrabody probes. Some embodiments of the present invention relate to a medical sonography procedure in which an endoscope is used for conveying an ultrasound transducer via a body lumen toward a targeted anatomic site.

An aspect of some embodiments of the present invention relates to a device for intrabody guiding, optionally disposable, that includes a catheter with a shape adjustable chamber, referred to herein as an adjustable chamber, that is placed at the distal end thereof and covers at least a distal end of an imager, such as an ultrasound catheter.

The adjustable chamber is designed to be filled with a wave conductive medium, such as an ultrasound conductive medium, that increases wave conductivity in the space between the ultrasound imager and a body tissue in proximity to a targeted anatomic site. The filling optionally adjusts the volume and/or the shape of the adjustable chamber to size and/or shape of a body lumen in proximity of a targeted anatomic site. This adjustment is optionally used to establish a contact with the inner walls of the body lumen and/or expand the lumen's diameter. In such a manner, the wave conductivity in the space between the imager and the inner walls increases and the targeted anatomic site may be imaged without the need to fill the whole body lumen with the wave conductive mediums. The filling of the adjustable chamber may be performed before, during, and/or after the insertion of the catheter into the body lumen.

The fact that the ultrasound catheter does not come in contact with the human body is an advantage as it may be not have to be cleaned or reprocessed between uses on different patients.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to FIG. 1 which is a schematic illustration of a tip of a device 100 with a catheter 102, a sheath 115, an adjustable chamber 104 that covers a portion of an ultrasound catheter 106, according to some embodiments of the present invention. As used herein, a catheter is an endoscopic tube, a bronchoscope, an endoscope, and/or any other device which is designed to introduce an endoscopic tool in a human body and/or being introduced in a human body.

The catheter 102 is optionally circular and hollow and covers at least a distal end of the ultrasound catheter 106. The catheter 102 allows an ultrasonic imager 108, such as an ultrasonic imaging scanner, to pass therethrough.

Optionally, the ultrasonic imaging scanner 108 comprises one or more ultrasound transducers 108, such as one or more linear arrays, phased arrays and/or transesophageal phased arrays and/or any other ultrasound generators, transmitters and/or sensors. For brevity, the one or more ultrasound transducers are referred to herein as an ultrasound transducer.

In an exemplary embodiment of the invention, the adjustable chamber 104 wraps the imager 108, which optionally partially or fully extends beyond a distal extremity of catheter 102. Optionally, adjustable chamber 104 is made of an elastic material, such as a thermoplastic elastomer, for example polyurethane.

The adjustable chamber 104 is filled with a wave conductive medium, such as an ultrasound conductive medium. The wave conductive medium may be, for example, water, saline solution, colloid, gel, or any combination thereof. The filling and/or the material of the adjustable chamber 104 may be performed and/or selected according to the impedance of the contacted tissue. In an exemplary embodiment of the invention, the wave conductive medium is delivered to the adjustable chamber 104 by a conduit. The conduit may be a designated conduit, such as a feeder and a channel, as shown at 110, for delivering the wave conductive medium from one end of the device 100 to the other and vice versa. Optionally, the conduit is the gap between the ultrasound catheter 106 and the catheter 102. Optionally, the conduit is detachable. Optionally, the conduit 110 is secured to an outer surface of the catheter 102, for example by attachments which do not substantially affect the passage of the conductive fluid. Optionally, the amount of the wave conductive medium that is delivered to and/or from the adjustable chamber 104 adjusts the volume of the adjustable chamber 104. Optionally, the wave conductive medium stretches the adjustable chamber 104 and allows it to establish physical contact with the inner walls of body lumens that have different perimeters and/or shapes. In such a manner, a physical contact with an area in the proximity of the targeted anatomical site may be established. Optionally, the adjustable chamber 104 is an inflatable assembly having inflated and deflated configurations. In an inflated configuration, the adjustable chamber 104 is optionally designed to establish physical contact with the inner walls of body lumens. For example, the diameter of the adjustable chamber 104 may be between 2 mm and 50 mm. In a deflated configuration, the diameter of the adjustable chamber 104 is smaller than the diameter of a working channel of an endoscope so as to allow the passage thereof therethrough. Optionally, when the adjustable chamber 104 is in a deflated state it does not apply pressure on the inner walls of the body lumens.

The inflatable adjustable chamber 104 may be used to increase ultrasound wave conductivity without moving ultrasound catheter 106. For example, if ultrasound transducer 108 is in the vicinity of the targeted anatomic site, adjustable chamber 104 may be filled by directing ultrasound conductive medium into adjustable chamber 104 to increase the contact between the outer surface of adjustable chamber 104 and the targeted anatomic site.

The inflating and deflating of the adjustable chamber 104 may allow maintaining uniform wave conductivity regardless of the diameter of the body lumens. The volume of the adjustable chamber may be adjusted to fit the perimeter of the body lumen in the proximity of the targeted anatomical site and assures physical contact that increases the quality of the image that is produced from the ultrasound transmissions of the ultrasound transducer 108. As the ultrasound transducer 108 may be positioned different distances from the targeted anatomical sites, device 100 may establish a physical contact with walls of lumens that have variable and/or non uniform perimeter.

In some embodiments of the present invention, the device 100 comprises a mechanism for extracting gas, such as air, from the adjustable chamber 104 and/or the conduits which are used for delivering the ultrasound conductive medium thereto and therefrom. In such a manner, pockets of gas which may reduce the quality of the ultrasound imaging may be avoided and/or reduced. For example, the mechanism of the described below piston is used for pumping gas from the adjustable chamber 104 when the ultrasound catheter cover is vertical and the distal end of the adjustable chamber 104 is positioned to face the ground. Then, the piston may be used for delivering the conductive fluid without or substantially without air, as described above. In another embodiment, the mechanism includes a piston, such as the piston that is described below. The piston is connected to a separate conduit that is positioned in the channels which are used for filling the adjustable chamber 104. The piston is used for venting out the gas when the ultrasound catheter cover is vertical and the distal end of the adjustable chamber 104 faces the top, for example while injecting the conductive fluid. Optionally, the separate conduit is connected to a valve that is controlled according to the orientation of the device 100. It should be noted that such a conduit may or may not be connected to the piston and/or to any other pump as long as the conduit and fluid injection and deflation system are resistant to gas influx.

Optionally, the adjustable chamber 104 and the walls of the catheter 102 are made of a material with a different elasticity coefficient. As a result, the filling of the catheter 102 with ultrasound conductive medium stretches the catheter 102 to a much lesser degree than the walls of the adjustable chamber 104, optionally in a manner that allows forward and back movement within the catheter 102. Such a movement may be taken into account when analyzing the signals of the ultrasonic imager 108. In another embodiment of the present invention, the catheter 102 and the adjustable chamber 104 are made from a material having a similar elasticity coefficient and the catheter 102 has walls which are thicker than the walls of the adjustable chamber 104, for example as shown at 114 and 116. Consequently, an ultrasound conductive medium delivered via the catheter 102 inflates adjustable chamber 104 without, or substantially without, changing the perimeter of the catheter 102. In such a manner, device 100 allows the extending of the volume of adjustable chamber 104 while the volume of catheter 102 does not change substantially and therefore does not apply pressure on the walls of the intrabody lumen through which it has been introduced. Alternatively, the material of catheter 102 and the material of adjustable chamber 104 have a different elasticity coefficient. In this manner, the introduction of conductive medium expands the adjustable chamber 104 without substantially expanding the perimeter of the catheter 102.

According to some embodiments of the present invention, catheter 102 is made of polyurethane and/or polyvinyl chloride (PVC). Alternatively, catheter 102 may be formed of a relatively rigid, optionally relatively thin, material, such as glycol-modified polyethylene terephthalate (PETG) and/or acrylic. Optionally, inner diameter 112 of catheter 102 measures about 3 millimeters, and is larger than the diameter of ultrasound catheter 106 which optionally measures 1 mm to 2 mm. Optionally, catheter 102 is made of an elastic material, such as a thermoplastic elastomer, for example polyurethane or C-Flex™ thermoplastic elastomer. Optionally, the thickness 114 of the walls of the catheter 102 is between 0.05 and 1.0 millimeters. It should be noted that the dimensions of inner diameter 112 and wall thickness 114 are merely exemplary.

Optionally, the adjustable chamber 104 is an integral part of the catheter 102 and is an extension thereof. Optionally, the adjustable chamber 104 is detachable from the catheter 102.

Optionally, the conduit 110, at the proximal extremity is connected to a pressure control device, such as a piston-cylinder device, which is controlled by a user to control the introduction of the ultrasound conductive medium to adjustable chamber 104.

Optionally, the piston is controlled by a user through an electronically controlled linear actuator. Optionally the piston-cylinder device is a syringe. Optionally, the syringe includes a barrel characterized by screw threads, which allows a user to rotate the barrel in and out of the syringe's cylinder, with a high degree of precision. Optionally, the conduit 110 is connected to a variable pressure regulator for controlling the inflation and deflation of adjustable chamber 104. For example, the variable pressure regulator may be of a common type where there is a spring loaded diaphragm, in which a pressure exerted by the spring on the diaphragm dictates a pressure of the ultrasound conductive medium flowing through conduit 110. Variable pressure regulators of this type are manufactured, for example, by Watts Regulator Company, and Fairchild Industrial Products Company.

Figure 2:
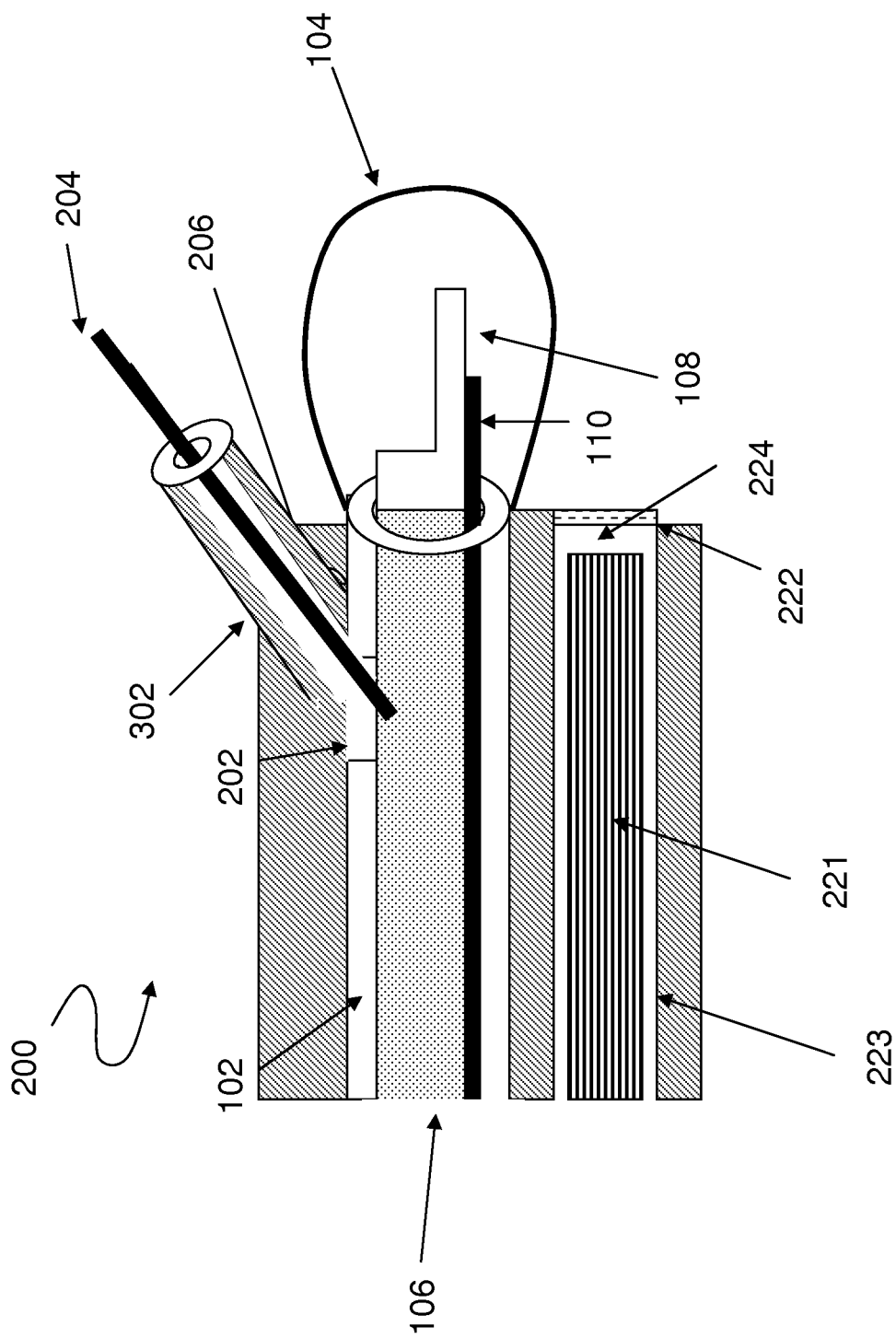
FIG. 2 is a schematic illustration of a tool deflector and a tip of a catheter characterized by an adjustable chamber and, according to some embodiments of the present invention.

Reference is now also made to FIG. 2 which is a schematic illustration of a device 200 for simultaneously introducing optical and ultrasound imagers, according to some embodiments of the present invention. The device 200 is characterized by a catheter 102, an adjustable chamber 104 and a tool deflector 206, and traversed by an endoscopic tool 204. As depicted in FIG. 2, device 200 may be comprised of an endoscope protective sheath 223 having a channel 224 with a window 222 at its distal end. In such an embodiment, device 200 may be used for introducing an optic imager, such as an optic fiber. Optionally, the window 222 is made of a clear rigid material, such as glass, Plexiglas, and/or polyester, for allowing the optic imager to capture video images. Optionally, the video imager is used for guiding the device 200 toward a targeted anatomic site.

Optionally, the device 200 has an aperture 202 that allows the passage of the endoscopic tool 204 toward an anatomical site. Optionally, device 200 further includes tool deflector 206, for changing the orientation of the endoscopic tool 204. Optionally, the tool deflector 206 is an electromechanical deflector, a cam type deflector, and/or an inflatable deflector, for example as described in US Patent Application 61/129,344 filed in Jun. 19, 2008, which is incorporated herein by reference.

Optionally, the tool deflector 206 is mounted on the outer surface of the intrabody guiding tube of the catheter 102, as pictured.

The incorporation of tool deflector 206 into device 200 may provide the endoscopic tool 204 an additional degree of freedom that decreases the dependency of the endoscopic tool 204 on the movement of ultrasound catheter 106. For example, the tool deflector 206 allows a change in the orientation of the endoscopic tool 204, independent of the movement of the intrabody guide tube of the catheter 102 and ultrasound catheter 106. Furthermore, the tool deflector 206 may divert the endoscopic tool 204 toward the targeted anatomic site without changing the orientation of the intrabody guide tube 102 and the ultrasound catheter 106, for example, if ultrasound catheter 106 is placed closely enough to a targeted anatomic site which is to be treated and/or probed by the endoscopic tool 204.

As depicted in FIG. 2, the catheter 102 covers at least a distal end of the ultrasound catheter 106, and provides tool deflector 206, to control an orientation of endoscopic tool 204. A real time image that is provided by ultrasound transducer 108 is optionally analyzed by an image processor in order to determine the orientation of the endoscopic tool 204. A processing unit is used for creating a graphic overlay representing a future trajectory of endoscopic tool 204. The graphic overlay is superimposed on the image, and helps a user to guide the endoscopic tool 204 toward the targeted anatomic site that is imaged by the ultrasound transducer 108.

Figure 3:
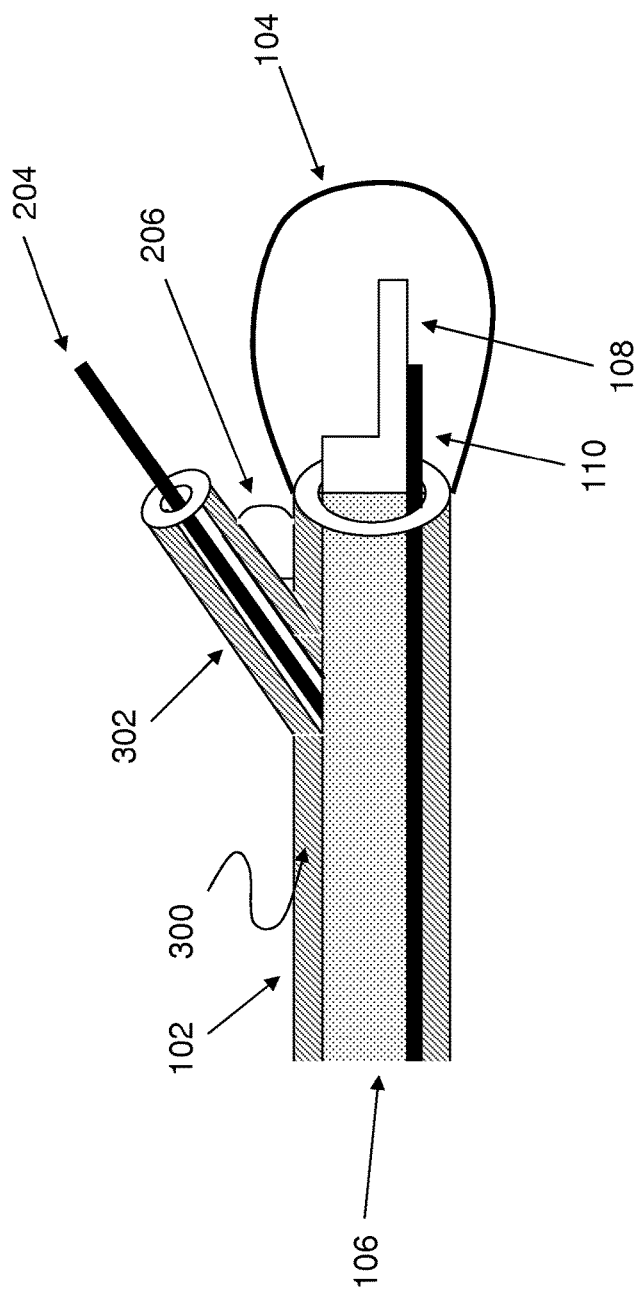
FIG. 3 is a schematic illustration of a tip of a catheter characterized by a sheath channel that contains at least a portion of an endoscopic tool, according to some embodiments of the present invention.

Reference is now also made to FIG. 3, which is a schematic illustration of a device 300 which has a sheath channel that covers at least a portion of an endoscopic tool 204, according to some embodiments of the present invention. In addition to elements described in FIG. 2, device 300 includes a working channel 302, which covers at least a portion of an endoscopic tool 204, and also serves to guide it. The sheath channel 302 comprises an aperture and/or a nozzle at the tip of the working channel 302 for allowing a distal tip of endoscopic tool 204 to directly contact the walls of a body lumen.

Optionally, working channel 302 terminates prior to the adjustable chamber 104. In such a manner, sheath channel 302 assures that the endoscopic tool 204 does not puncture the adjustable chamber 104.

Optionally, the working channel 302 is an integral part of the catheter 102.

Figure 4:
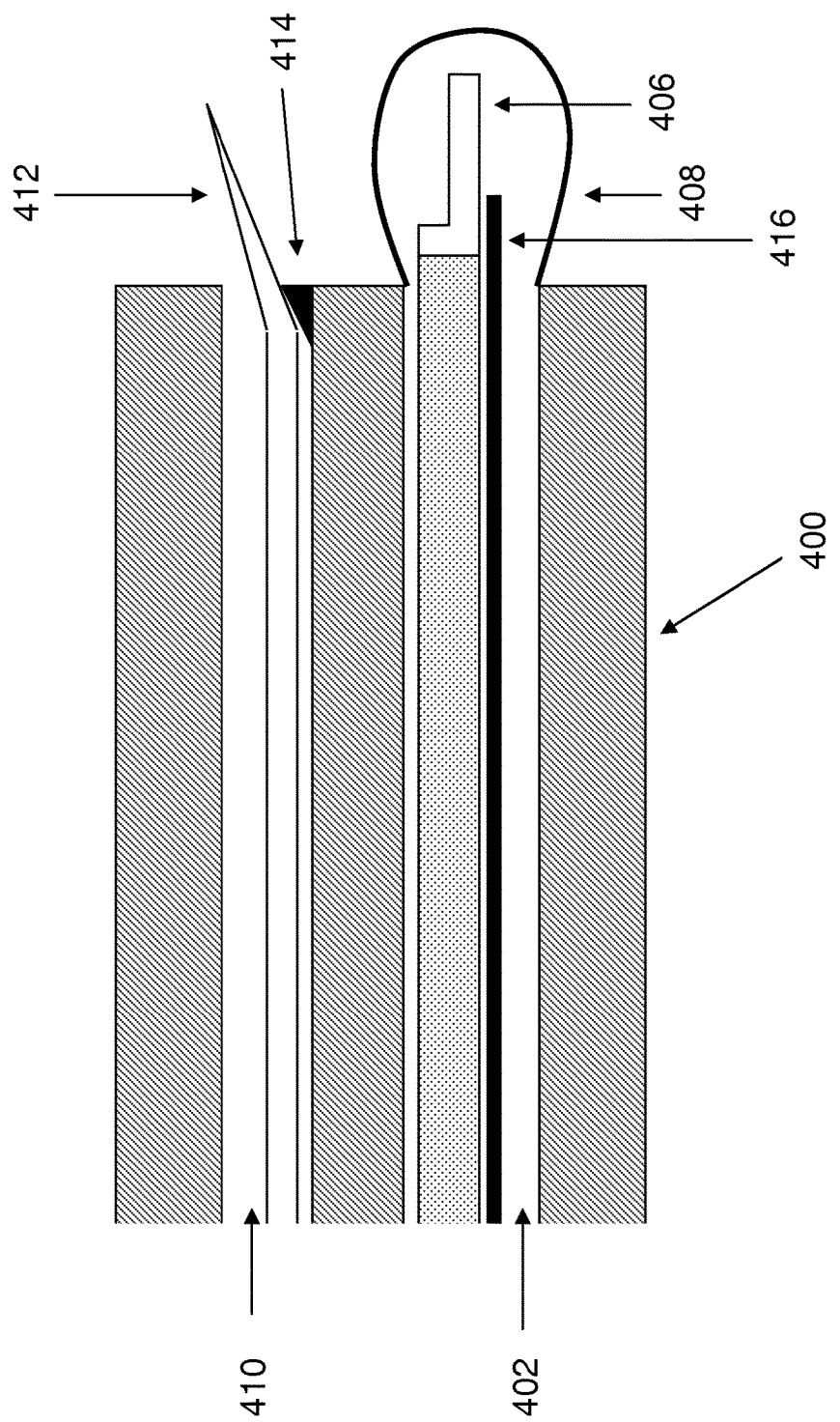
FIG. 4 is a schematic illustration of an endoscopic insertion tube, characterized by an adjustable chamber designed to be filled with a wave conductive medium, according to some embodiments of the present invention.

Reference is now also made to FIG. 4 which is a schematic illustration of a device 400 with an integrated channel 410 for conducting a deflectable endoscopic tool 412, according to some embodiments of the present invention. The device 400 includes the channel 402 for allowing an ultrasonic imaging scanner 406 to pass therethrough and an adjustable chamber 408 that covers the distal opening thereof and functions similarly to the described above. The adjustable chamber 408 is optionally attached by a rubber-band or a metal band to end of the device 400.

As depicted in FIG. 4, the device 400 further includes a second channel 410 for housing an endoscopic tool 412. The second channel 410 has a tool deflector 414 which is placed at a distal end thereof and allows changing the orientation of endoscopic tool 412. The tool deflector 414 may be placed inside the second channel 410, outside second channel 410, or both inside and outside second channel 410. Optionally, the tool deflector 414 is one of the tool deflectors described above.

Optionally, ultrasound conductive medium is conducted toward and/or from the adjustable chamber 408, via a channel 402, similarly to the described above. Optionally, device 400 includes a ultrasound conductive medium channel 416, for conducting the ultrasound conductive medium toward and/or from adjustable chamber 408. Optionally, ultrasound conductive medium is directed into and out of adjustable chamber 408, using units, such as a piston-cylinder device, described above.

As described above, adjustable chamber 408 is optionally a disposable adjustable chamber that covers the ultrasonic imaging scanner 406. In such a manner, the ultrasonic imaging scanner 406 is not contaminated during the endoscopy procedure and therefore the need to sterilize and/or decontaminate it is reduced and/or eliminated.

Optionally, the endoscope to which device 400 is used in conjunction with is a bronchoscope which is used for reaching remote areas within the airways and probing and/or treating the above areas.

Reference is now made to FIG. 5, which is a flowchart illustrating a method 500 for imaging a targeted anatomic site within a body lumen, according to some embodiments of the present invention. At 502, an endoscope is used for conveying an ultrasound transducer in an adjustable chamber via a body lumen toward a targeted anatomic site, as described above. Optionally, the device is one of the devices which are depicted in FIGS. 1 and 4. As shown at 504, the ultrasound transducer is guided by a user toward a desired targeted anatomic site, for example by manipulations of the endoscope in a body lumen. As shown at 506, an ultrasound conductive medium is introduced into or aspirated from the adjustable chamber, for example as shown at numeral 104 of FIGS. 1, 2, and 3, or numeral 408 of FIG. 4. The ultrasound conductive medium extends the adjustable chamber so as to increase the wave conductivity in the space between the imager and the inner wall of a lumen, optionally as further described above. As shown at 508, the wave conductivity allows the ultrasound transducer to image the targeted anatomic site. As described above, the adjustable chamber may be deflated and/or inflated to refine the ultrasonic imaging of the targeted anatomic site.

It is expected that during the life of a patent maturing from this application many relevant apparatuses and methods will be developed and the scope of the term ultrasonic imaging scanner and ultrasound transducer is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for passage of an ultrasound catheter, said device comprising:
    a first channel configured for traversing of at least a portion of the ultrasound catheter therethrough, said ultrasound catheter having an ultrasound imager at an opened distal end thereof;
    a second channel configured for traversing of an endoscopic tool therethrough;
    an adjustable chamber in communication with said ultrasound catheter and positioned at a furthest tip of the opened distal end of said device, the adjustable chamber covering at least the opened distal end of the device and configured for enclosing said ultrasound imager, said adjustable chamber being configured for being adjusted by a wave conductive medium introduced thereto via said first channel; and a deflector mounted at said opened distal end of said device, said deflector configured to deflect said second channel in a fixed direction from a longitudinal axis of said first channel by an angle that causes said endoscopic tool to divert toward a targeted anatomical site without changing the orientation of said ultrasound catheter and said imager in said adjustable chamber of said device when said endoscopic tool is extended out of said opened distal end of said device beyond the range of said adjustable chamber toward the targeted anatomical site.

2. The device of claim 1, wherein said device is a disposable sheath configured for containing an endoscopic tool.

3. The device of claim 1, wherein said device is configured for insertion into a body lumen in proximity to said targeted anatomical site, said adjustable chamber is configured for being stretched to increase wave conductivity in a space between said targeted anatomic site and said imager.

4. The device of claim 1, wherein said adjustable chamber is made of a non stretchable material and said adjustable chamber includes a volume configured for being inflated to increase wave conductivity in a space between said targeted anatomic site and said imager.

5. The device of claim 3, wherein said wave conductivity is increased by reducing the space between an outer surface of said adjustable chamber and at least one inner wall of said body lumen.

6. The device of claim 3, wherein said imager comprises at least one ultrasound transducer and said wave conductivity being an ultrasonic conductivity.

7. The device of claim 1, wherein said adjustable chamber is detachable from said device.

8. The device of claim 1, wherein said device is disposable.

9. The device of claim 1, wherein said adjustable chamber and said device are integrally formed.

10. The device of claim 1, further comprising a separate conduit configured for introducing said conductive medium.

11. The device of claim 1, wherein said device includes a sheath channel located on a surface of said device and configured for preventing puncturing said adjustable chamber by said endoscopic tool.

12. The device of claim 1, further comprising a mechanism configured for reducing the amount of gas in said adjustable chamber.

13. A method for imaging a targeted anatomic site within a body lumen, comprising:

guiding a device, which has received an ultrasound catheter with an imager at a distal end thereof, toward a proximity of the targeted anatomic site via a body lumen, said device including a first channel connected to an adjustable chamber positioned at a forward-facing portion of an opened distal end of said device, the adjustable chamber covering at least the opened distal end of the device and enclosing said imager;

increasing wave conductivity between at least one inner wall of said body lumen and said imager;

using said imager for imaging the targeted anatomic site through said wave conductive medium and said adjustable chamber;

guiding an endoscopic tool through a second channel of said device; and diverting said endoscopic tool toward said anatomic site by a deflector deflecting said second channel in a fixed direction from a longitudinal axis of said first channel to divert said endoscopic tool toward said anatomic site without changing the orientation of said ultrasound catheter and imager in said opened distal end of said device;

wherein said diverted endoscopic tool extends from said device beyond the range of said adjustable chamber;

wherein said deflector is mounted at said opened distal end of said device.

14. The method of claim 13, wherein said increasing comprises reducing a space between an outer surface of said adjustable chamber and at least one inner wall of a body lumen in proximity to said targeted anatomic site.

15. The method of claim 13, wherein said increase is a product of establishing a physical contact between at least one inner wall of said body lumen and said adjustable chamber.

16. The method of claim 13, wherein said imager comprises at least one ultrasound transducer and said wave conductivity being an ultrasonic conductivity.

17. An endoscope for imaging an anatomic site in proximity to a body lumen, comprising:

a device having an open distal end and configured for insertion into the body lumen, said device having a first channel for traversing an ultrasound catheter having an ultrasound imager and a wave conductive medium therethrough and a second channel for traversing an endoscopic tool therethrough; and an adjustable chamber positioned at a furthest tip of and in communication with said open distal end, said adjustable chamber configured for enclosing at least the opened distal end of the device and said ultrasound imager when said ultrasound imager is inside said adjustable chamber;

wherein said adjustable chamber is configured for being filled with said wave conductive medium to increase wave conductivity in a space between the anatomic site and said ultrasound imager; and wherein said device comprises a deflector mounted at said open distal end to deflect at least a bottom surface of said second channel in an angle that causes said endoscopic tool to divert toward a targeted anatomical site without changing the orientation of said ultrasound catheter in said open distal end of the device and allows said endoscopic tool to extend out of said open distal end of said device, beyond the range of said adjustable chamber.

18. The endoscope of claim 17, further comprising a pressure device in communication with said device for controlling said wave conductive medium.

19. The endoscope of claim 17, wherein said adjustable chamber is configured for being attached in a detachable manner to said device.

20. The endoscope of claim 17, wherein said deflector is positioned in said device at said open distal end.

21. The device of claim 1, wherein said deflector is positioned in said device at said opened distal end.

* * * * *